(12) United States Patent
Brown et al.

(10) Patent No.: US 9,421,092 B2
(45) Date of Patent: Aug. 23, 2016

(54) AUTOMATED INTRAOCULAR LENS INJECTOR DEVICE

(75) Inventors: Kyle Brown, Fort Worth, TX (US); David A. Downer, Fort Worth, TX (US); Sushant Muchhala, Kennedale, TX (US); Stephen J. Van Noy, Southlake, TX (US); Dengzhua (Dan) Yan, Arlington, TX (US); Marshall K. Proulx, Keller, TX (US)

(73) Assignee: Alcon Research, Ltd., Forth Worth, TX (US)

( * ) Notice: Subject to any disclaimer, the term of this patent is extended or adjusted under 35 U.S.C. 154(b) by 1233 days.

(21) Appl. No.: 12/702,465

(22) Filed: Feb. 9, 2010

(65) Prior Publication Data

US 2010/0204705 A1 Aug. 12, 2010

Related U.S. Application Data

(60) Provisional application No. 61/151,712, filed on Feb. 11, 2009.

(51) Int. Cl.
*A61F 2/16* (2006.01)

(52) U.S. Cl.
CPC .................. *A61F 2/1678* (2013.01)

(58) Field of Classification Search
CPC .... A61F 2/1662; A61F 2/167; A61F 2/1675; A61F 2/1678
USPC ........................ 606/107, 108; 623/6.11, 6.12
See application file for complete search history.

(56) References Cited

U.S. PATENT DOCUMENTS

| 4,573,998 A | 3/1986 | Mazzocco |
|---|---|---|
| 4,619,657 A | 10/1986 | Keates et al. |

(Continued)

FOREIGN PATENT DOCUMENTS

| AU | 728443 B2 | 1/2001 |
|---|---|---|
| DE | 4301573 | 7/1994 |

(Continued)

OTHER PUBLICATIONS

Abstract of article entitled "Implantation of the AcrySof MA30BA lens using the Monarch System" by Barakova D., original article found in Cesk slov Oftalmol, 2002 58(3), at p. 149-152, found in PubMed database at http://www.ncbi.nlm.nih.gov/pubmed/12087658 (1 page).

(Continued)

*Primary Examiner* — Jonathan Miles
(74) *Attorney, Agent, or Firm* — Darien Reddick

(57) ABSTRACT

An intraocular lens injector cartridge assembly contains a pre-loaded lens and an integral lens-contacting plunger rod. Configured for removably mating with an injector handpiece, the cartridge assembly is suitable for use with either manual or automated injector systems. The injector cartridge assembly includes a tubular body having a longitudinal bore extending between a distal end and a proximal end, an IOL disposed within said longitudinal bore, and a lens-contacting plunger rod retained within said bore, between the IOL and the proximal end of the tubular body. The lens-contacting plunger rod is configured for translation along the longitudinal bore upon engagement by an injector rod introduced by the injector handpiece into the proximal end of the tubular body, so that the IOL is folded and ejected from the distal end of the tubular body by the translation of the lens-contacting plunger rod.

14 Claims, 4 Drawing Sheets

(56) References Cited

U.S. PATENT DOCUMENTS

| | | |
|---|---|---|
| 4,681,102 A | 7/1987 | Bartell |
| 4,747,404 A | 5/1988 | Jampel et al. |
| 4,834,094 A | 5/1989 | Patton et al. |
| 4,836,201 A | 6/1989 | Patton et al. |
| 4,919,130 A | 4/1990 | Stoy et al. |
| 4,934,363 A | 6/1990 | Smith et al. |
| 4,960,557 A | 10/1990 | Sorensen |
| 5,026,396 A | 6/1991 | Darin |
| 5,098,439 A | 3/1992 | Hill et al. |
| 5,190,552 A | 3/1993 | Kelman |
| 5,275,604 A | 1/1994 | Rheinish et al. |
| 5,304,182 A | 4/1994 | Rheinish et al. |
| 5,354,333 A | 10/1994 | Kammann et al. |
| 5,397,313 A | 3/1995 | Gross |
| 5,425,734 A | 6/1995 | Blake |
| 5,444,183 A | 8/1995 | Gehrs et al. |
| 5,464,396 A | 11/1995 | Barta et al. |
| 5,468,246 A | 11/1995 | Blake |
| 5,494,484 A | 2/1996 | Feingold |
| 5,496,278 A | 3/1996 | Buff |
| 5,496,328 A | 3/1996 | Nakajima et al. |
| 5,499,987 A | 3/1996 | Feingold |
| 5,578,042 A | 11/1996 | Cumming |
| 5,582,614 A | 12/1996 | Feingold |
| 5,607,433 A | 3/1997 | Polla et al. |
| 5,616,148 A | 4/1997 | Eagles et al. |
| 5,620,450 A | 4/1997 | Eagles et al. |
| 5,629,577 A | 5/1997 | Polla et al. |
| 5,643,275 A | 7/1997 | Blake |
| 5,643,276 A | 7/1997 | Zaleski |
| 5,653,715 A | 8/1997 | Reich et al. |
| 5,653,753 A | 8/1997 | Brady et al. |
| 5,716,364 A | 2/1998 | Makker et al. |
| 5,728,102 A | 3/1998 | Feingold et al. |
| 5,735,858 A | 4/1998 | Makker et al. |
| 5,772,666 A | 6/1998 | Feingold et al. |
| 5,776,138 A | 7/1998 | Vidal et al. |
| 5,800,441 A | 9/1998 | Polla et al. |
| 5,800,442 A | 9/1998 | Wolf et al. |
| 5,803,925 A | 9/1998 | Yang et al. |
| 5,807,400 A | 9/1998 | Eagles |
| 5,810,834 A | 9/1998 | Heyman |
| 5,820,373 A | 10/1998 | Okano et al. |
| 5,860,986 A | 1/1999 | Reich et al. |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,891,153 A | 4/1999 | Peterson |
| 5,944,725 A | 8/1999 | Cicenas et al. |
| 5,947,976 A | 9/1999 | Van Noy et al. |
| 6,010,510 A | 1/2000 | Brown et al. |
| 6,042,587 A | 3/2000 | Polla et al. |
| 6,056,757 A | 5/2000 | Feingold |
| 6,056,758 A | 5/2000 | Vidal et al. |
| 6,083,231 A | 7/2000 | Van Noy et al. |
| 6,140,602 A | 10/2000 | Costin |
| 6,143,001 A | 11/2000 | Brown et al. |
| 6,162,229 A | 12/2000 | Feingold et al. |
| 6,162,230 A | 12/2000 | Polla et al. |
| 6,163,963 A | 12/2000 | Huang |
| 6,179,843 B1 | 1/2001 | Weiler |
| 6,228,094 B1 | 5/2001 | Erdman |
| 6,254,607 B1 | 7/2001 | Makker et al. |
| 6,276,014 B1 | 8/2001 | Lee |
| 6,334,862 B1 | 1/2002 | Vidal et al. |
| 6,355,046 B2 | 3/2002 | Kikuchi et al. |
| 6,423,035 B1 | 7/2002 | Das et al. |
| 6,447,519 B1 | 9/2002 | Brady et al. |
| 6,471,708 B2 | 10/2002 | Green |
| 6,497,708 B1 | 12/2002 | Cumming |
| 6,500,181 B1 | 12/2002 | Portney |
| 6,503,275 B1 | 1/2003 | Cumming |
| 6,537,283 B2 | 3/2003 | Van Noy |
| 6,558,395 B2 | 5/2003 | Hjertman et al. |
| 6,592,591 B2 | 7/2003 | Polla et al. |
| 6,607,537 B1 | 8/2003 | Binder |
| 6,635,731 B2 | 10/2003 | Mentak |
| 6,666,871 B2 | 12/2003 | Kikuchi et al. |
| 6,685,740 B2 | 2/2004 | Figueroa et al. |
| 6,887,221 B1 | 5/2005 | Baillargeon et al. |
| 6,899,717 B2 | 5/2005 | Weber et al. |
| 6,923,815 B2 | 8/2005 | Brady et al. |
| 6,964,648 B2 | 11/2005 | Talling et al. |
| 6,976,989 B1 | 12/2005 | Vincent |
| 7,014,641 B2 | 3/2006 | Kobayashi et al. |
| 7,042,180 B2 | 5/2006 | Terry et al. |
| 7,097,649 B2 | 8/2006 | Meyer |
| 7,131,976 B2 | 11/2006 | Kobayashi et al. |
| 7,156,854 B2 | 1/2007 | Brown et al. |
| 7,156,855 B2 | 1/2007 | Oda |
| 7,189,218 B2 | 3/2007 | Lichtenberg |
| 7,279,006 B2 | 10/2007 | Vincent |
| 7,422,604 B2 | 9/2008 | Vaquero et al. |
| 7,429,263 B2 | 9/2008 | Vaquero et al. |
| 8,000,249 B2 | 8/2011 | Nagy et al. |
| 8,109,938 B2 | 2/2012 | Pessin |
| 2001/0007075 A1 | 7/2001 | Hjertman et al. |
| 2002/0022881 A1 | 2/2002 | Figueroa et al. |
| 2003/0040755 A1 | 2/2003 | Meyer |
| 2003/0135221 A1 | 7/2003 | Sabet |
| 2003/0139749 A1 | 7/2003 | Kikuchi et al. |
| 2003/0212406 A1 | 11/2003 | Kobayashi et al. |
| 2003/0212409 A1 | 11/2003 | Kobayashi et al. |
| 2004/0054374 A1 | 3/2004 | Weber et al. |
| 2004/0059343 A1 | 3/2004 | Shearer et al. |
| 2004/0087896 A1 | 5/2004 | Wise et al. |
| 2004/0097956 A1 | 5/2004 | Oda |
| 2004/0127911 A1 | 7/2004 | Figueroa et al. |
| 2004/0147938 A1 | 7/2004 | Dusek et al. |
| 2004/0160575 A1 | 8/2004 | Ayton et al. |
| 2004/0199174 A1 | 10/2004 | Herberger et al. |
| 2004/0215207 A1 | 10/2004 | Cumming |
| 2004/0238392 A1 | 12/2004 | Peterson et al. |
| 2005/0029976 A1 | 2/2005 | Terry et al. |
| 2005/0049605 A1 | 3/2005 | Vaquero et al. |
| 2005/0049606 A1 | 3/2005 | Vaquero et al. |
| 2005/0065534 A1 | 3/2005 | Hohl |
| 2005/0143750 A1 | 6/2005 | Vaquero |
| 2005/0149056 A1 | 7/2005 | Rathert |
| 2005/0149057 A1 | 7/2005 | Rathert |
| 2005/0203619 A1 | 9/2005 | Altmann |
| 2005/0222578 A1 | 10/2005 | Vaquero |
| 2005/0222579 A1 | 10/2005 | Vaquero et al. |
| 2006/0066962 A1 | 3/2006 | Totzeck et al. |
| 2006/0085013 A1 | 4/2006 | Dusek et al. |
| 2006/0167466 A1 | 7/2006 | Dusek |
| 2006/0184181 A1 | 8/2006 | Cole et al. |
| 2006/0200167 A1 | 9/2006 | Peterson et al. |
| 2006/0229633 A1 | 10/2006 | Shepherd |
| 2006/0229634 A1 | 10/2006 | Shepherd |
| 2006/0235429 A1 | 10/2006 | Lee et al. |
| 2006/0284581 A1 | 12/2006 | Mullin |
| 2007/0005135 A1 | 1/2007 | Makker et al. |
| 2007/0050023 A1 | 3/2007 | Bessiere et al. |
| 2007/0060925 A1 | 3/2007 | Pynson |
| 2007/0150056 A1 | 6/2007 | Meyer |
| 2007/0173860 A1 | 7/2007 | Iwaski |
| 2008/0033449 A1 | 2/2008 | Cole et al. |
| 2008/0039862 A1 | 2/2008 | Tran |
| 2008/0058830 A1 | 3/2008 | Cole et al. |
| 2008/0097459 A1 | 4/2008 | Kammerlander et al. |
| 2008/0097460 A1 | 4/2008 | Boukhny et al. |
| 2008/0119865 A1 | 5/2008 | Meunier et al. |
| 2008/0200920 A1 | 8/2008 | Downer |
| 2008/0200921 A1 | 8/2008 | Downer |
| 2008/0221584 A1 | 9/2008 | Downer |
| 2008/0221585 A1 | 9/2008 | Downer |
| 2008/0255577 A1 | 10/2008 | Downer |
| 2008/0312661 A1 | 12/2008 | Downer et al. |
| 2009/0043313 A1 | 2/2009 | Ichinohe et al. |
| 2009/0112223 A1 | 4/2009 | Downer |
| 2009/0171366 A1 | 7/2009 | Tanaka |
| 2009/0204123 A1 | 8/2009 | Downer |

(56) References Cited

U.S. PATENT DOCUMENTS

| | | |
|---|---|---|
| 2009/0216244 A1 | 8/2009 | Pynson |
| 2010/0094309 A1 | 4/2010 | Boukhny et al. |
| 2010/0121340 A1 | 5/2010 | Downer |

FOREIGN PATENT DOCUMENTS

| | | |
|---|---|---|
| DE | 19752076 A1 | 5/1999 |
| EP | 0174917 A1 | 3/1986 |
| EP | 0270257 A1 | 6/1988 |
| EP | 0363213 A2 | 4/1990 |
| EP | 0477466 A1 | 6/1996 |
| EP | 0820211 A1 | 1/1998 |
| EP | 0858304 A1 | 8/1998 |
| EP | 0962195 A1 | 12/1999 |
| EP | 1011561 A1 | 6/2000 |
| EP | 1076408 A2 | 2/2001 |
| EP | 1332731 A1 | 8/2003 |
| EP | 1360944 A2 | 11/2003 |
| EP | 1481652 A1 | 12/2004 |
| EP | 1661533 | 5/2006 |
| EP | 1832247 A1 | 9/2007 |
| EP | 1849436 A1 | 10/2007 |
| EP | 1891911 A1 | 2/2008 |
| EP | 1958593 A1 | 8/2008 |
| EP | 2062552 A1 | 5/2009 |
| FR | 2820633 | 8/2002 |
| GB | 2224214 A | 5/1990 |
| JP | 1176288 | 12/1989 |
| JP | H09-506285 | 2/1996 |
| JP | 10309294 | 11/1998 |
| JP | 10511876 | 11/1998 |
| JP | 10512460 | 11/1998 |
| JP | 2000025073 | 1/2000 |
| JP | 2000513955 T2 | 10/2000 |
| JP | 2003048488 A2 | 2/2003 |
| JP | 2003070829 | 3/2003 |
| JP | 2003325569 | 11/2003 |
| JP | 3664444 B2 | 6/2005 |
| JP | 2006006817 A2 | 1/2006 |
| JP | 2006014962 | 1/2006 |
| JP | 2006181269 A2 | 7/2006 |
| JP | 2006522674 T2 | 10/2006 |
| JP | 2007055057 | 3/2007 |
| JP | 2007215990 A2 | 8/2007 |
| RU | 2138232 | 9/1999 |
| RU | 2171100 | 7/2001 |
| RU | 2238283 C2 | 10/2004 |
| RU | 2242956 | 12/2004 |
| RU | 2375992 C2 | 12/2009 |
| SU | 1440496 | 11/1988 |
| WO | 9420027 A1 | 9/1994 |
| WO | 9610372 A1 | 4/1996 |
| WO | WO 96/10372 | 4/1996 |
| WO | 9620662 A1 | 7/1996 |
| WO | WO 96/20662 | 7/1996 |
| WO | 9628122 A1 | 9/1996 |
| WO | WO 96/28122 | 9/1996 |
| WO | 9629956 A1 | 10/1996 |
| WO | WO 96/29956 | 10/1996 |
| WO | 9715253 A1 | 5/1997 |
| WO | WO 97/15253 | 5/1997 |
| WO | 9726841 A2 | 7/1997 |
| WO | 9805281 A1 | 2/1998 |
| WO | 9812969 A1 | 4/1998 |
| WO | 9815244 A1 | 4/1998 |
| WO | 98015244 | 4/1998 |
| WO | 9820819 A1 | 5/1998 |
| WO | 0040175 A1 | 7/2000 |
| WO | WO 00/40175 | 7/2000 |
| WO | 0062712 A1 | 10/2000 |
| WO | WO 00/62712 | 10/2000 |
| WO | 2004091447 A2 | 10/2004 |
| WO | 2005020853 A2 | 3/2005 |
| WO | 2005023154 A2 | 3/2005 |
| WO | WO 2005/018515 | 3/2005 |
| WO | 2005023154 A3 | 6/2005 |
| WO | 2005102223 A1 | 11/2005 |
| WO | 2006059183 A1 | 6/2006 |
| WO | 2006070628 A1 | 7/2006 |
| WO | WO 2006/070561 | 7/2006 |
| WO | 2006080191 A1 | 8/2006 |
| WO | 2006113138 A1 | 10/2006 |
| WO | 2006113357 A2 | 10/2006 |
| WO | 2007054645 A2 | 5/2007 |
| WO | 2010044974 A1 | 4/2010 |

OTHER PUBLICATIONS

International Search Report for PCT/US2010/023544, Publication No. WO2010/093593, dated May 28, 2010, 4 pages.

PCT International Preliminary Report on Patentability and Written Opinion, PCT/US2010/023544, dated Aug. 16, 2011, 4 pages.

European Search Report for Application No. 08102172.7, Publication No. 1980219, dated Oct. 15, 2008, 5 pages.

International Search Report for PCT/US2009/057,083, Filed Sep. 16, 2009, Publication No. WO2010/044,974, Published Apr. 22, 2010, dated Dec. 30, 2009, 5 pages.

International Preliminary Report on Patentability with Written Opinion, dated Apr. 19, 2011, Application No. PCT/US2009/057083, Filed Sep. 16, 2009, Publication No. WO2010/044,974, Published Apr. 22, 2010, 7 pages.

International Search Report for PCT/US2011/032708, Publication No. WO2011/133427, dated Jun. 29, 2011, 2 pages.

Written Opinion of the International Searching Authority, International Application No. PCT/US2011/032708, Jun. 29, 2011, 4 pages.

European Search Report for Application No. 07114085.9, Publication No. EP1891911, dated Jan. 14, 2008, 2 pages.

European Search Report for Application No. 08100876.5, Publication No. EP1958593, dated Apr. 22, 2008, 2 pages.

European Search Report for Application No. 09154535.0, Publication No. EP2062552, dated Apr. 15, 2009, 2 pages.

International Search Report for PCT/US2012/030147, Publication No. WO2012/129419, dated Jul. 13, 2010, 2 pages.

Extended European Search Report for Application No. 11772480.7, Publication No. EP2528561, dated Oct. 2, 2013, 5 pages.

PCT International Preliminary Report on Patentability and Written Opinion, PCT/US2012/030147, filed Mar. 22, 2012, Publication No. 2012/129,419, Published Sep. 27, 2012, dated Sep. 24, 2013, 9 pages.

Shao; "Direct Back EMF Detection Method for Sensorless Brushless DC (BLDC) Motor Drives"; Virginia Polytechnic Institute and State University, Blacksburg, Virginia; Sep. 2003 (http://scholar.lib.vt.edu/theses/available/etd-09152003-171904/unrestricted/T.pdf); 91 pages.

Extended European Search Report for Application No. EP12760022.9, Publication No. EP2675393, dated Sep. 3, 2014, 7 pages.

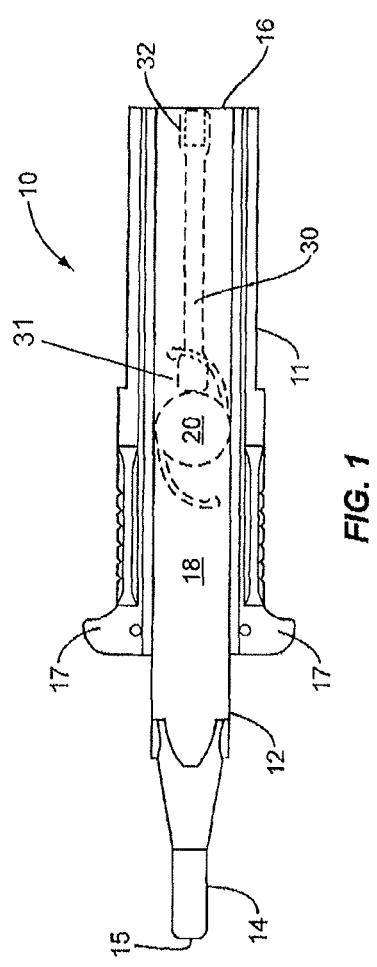
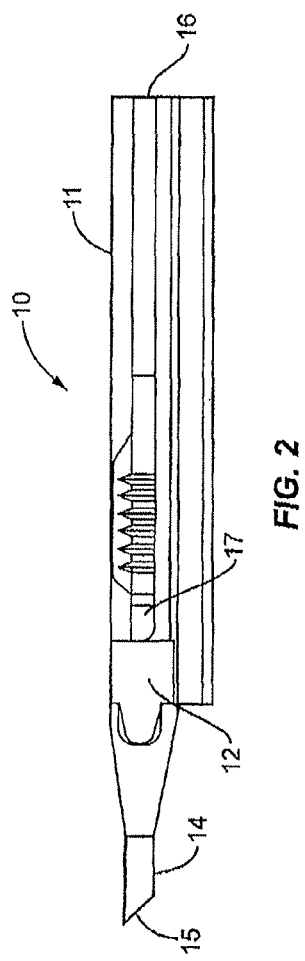
FIG. 1
FIG. 2

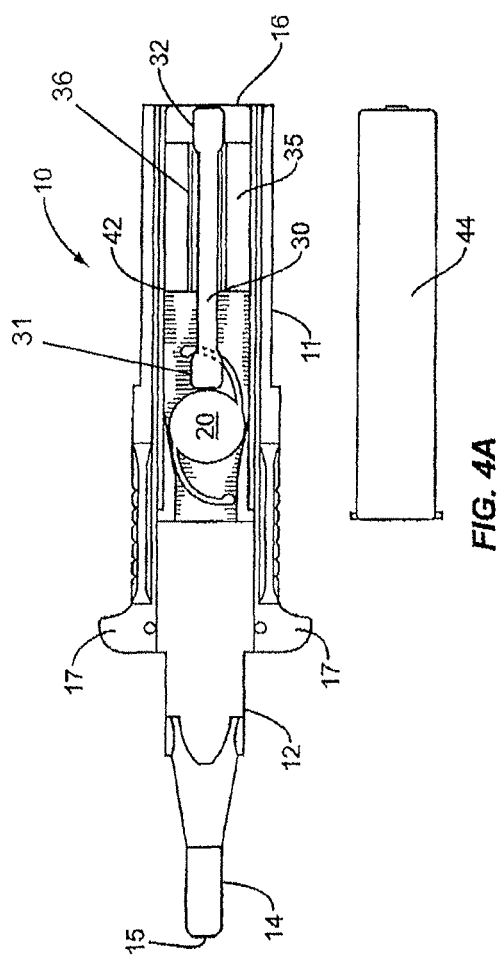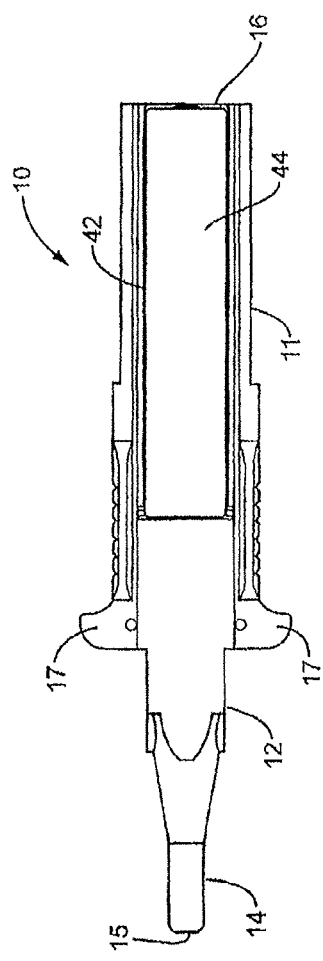
FIG. 4A
FIG. 4B

AUTOMATED INTRAOCULAR LENS INJECTOR DEVICE

CROSS REFERENCE TO RELATED APPLICATIONS

This application claims benefit of U.S. Provisional Application Ser. No. 61/151,712, filed Feb. 11, 2009.

TECHNICAL FIELD

The present invention relates generally to devices and techniques for delivering an intraocular lens (IOL) into an eye and more particularly to cartridges used for shipping and for injection of the IOLs.

BACKGROUND

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is then replaced by the IOL.

The IOL is injected into the eye through the same small incision used to remove the diseased lens. An insertion cartridge of an IOL injector is loaded with the IOL, the tip of the insertion cartridge is inserted into the incision, and the lens is delivered into the eye.

Many IOLs manufactured today are made from a polymer with specific characteristics. These characteristics allow the lens to be folded for insertion through a very small incision; the lens unfolds into its proper shape after delivery into the eye. Injector cartridges that fold the lens and provide a relatively small diameter lumen through which the lens may be pushed into the eye, usually by a soft tip plunger, are commonly used. Some of these cartridges are described in U.S. Pat. No. 5,947,976, issued Sep. 7, 1999 to Van Noy et al., and in U.S. Pat. No. 6,537,283, issued Mar. 25, 2003 to Van Noy; the entire contents of each of these patents is incorporated herein by reference. Other cartridges and injector devices are illustrated in U.S. Pat. No. 4,681,102 (Bartell), U.S. Pat. Nos. 5,494,484 and 5,499,987 (Feingold), U.S. Pat. Nos. 5,616,148 and 5,620,450 (Eagles, et al.), U.S. Pat. No. 5,275,604 (Rheinish, et al.), and U.S. Pat. No. 5,653,715 (Reich, et al.) the entire contents of each of these documents are also incorporated herein by reference to provide context and technical background for the disclosure that follows. Notwithstanding the various designs disclosed in these references, improvements in IOL injector cartridges and IOL injection techniques are still needed.

SUMMARY

An intraocular lens injector cartridge assembly containing a pre-loaded lens and an integral lens-contacting plunger rod is disclosed. The cartridge assembly is configured for removably mating with an injector handpiece, and is thus suitable for use with either manual or automated injector systems. An exemplary embodiment of an intraocular lens injector cartridge assembly includes a tubular body having a longitudinal bore extending between a distal end and a proximal end, an intraocular lens disposed within said longitudinal bore, and a lens-contacting plunger rod retained substantially within said bore, between the intraocular lens and the proximal end of the tubular body. The lens-contacting plunger rod is configured for translation along the longitudinal bore upon engagement by an injector rod introduced by the injector handpiece into the proximal end of the tubular body, so that the intraocular lens is folded and ejected from the distal end of the tubular body by the translation of the lens-contacting plunger rod. In some embodiments, the cartridge assembly comprises a plunger guide disposed within the longitudinal bore and at least partially surrounding the circumference of the lens-contacting plunger rod.

Various embodiments of the cartridge assembly may further include one or more grips protruding from the tubular body, for engagement with the injector handpiece. In some embodiments, the tubular body comprises an opening disposed on a first face of the tubular body for installing at least one of the intraocular lens and the lens-contacting plunger rod, and a cover installed over said opening. The cover is connected to the tubular body by a hinge at one end of the cover, in some of these embodiments; in these and other embodiments the tubular body may comprise one or more retaining features proximate to the opening, so that the cover can be configured to snap fit into the one or more retaining features.

Of course, those skilled in the art will appreciate that the present invention is not limited to the above features, advantages, contexts or examples, and will recognize additional features and advantages upon reading the following detailed description and upon viewing the accompanying drawings.

BRIEF DESCRIPTION OF THE DRAWINGS

FIG. 1 is a plan view of an exemplary disposable, pre-loaded, intraocular lens injector cartridge assembly.

FIG. 2 is an elevation view of the cartridge assembly of FIG. 1.

FIGS. 4A and 4B illustrate another exemplary IOL injector cartridge assembly.

DETAILED DESCRIPTION

Many conventional intraocular lens (IOL) injector cartridges, including several of those described in the U.S. patents discussed above, are manually loaded with an IOL shortly before the injection procedure, and attached to an injector handpiece. The handpiece, which may be manually or electrically powered, includes a lens contacting plunger that is forced into and through the injector cartridge, folding the lens and ejecting the lens into the eye from the tip, or "distal" end, of the injector cartridge. In addition to the inconvenience and potential complications associated with loading the IOL, those skilled in the art will appreciate that another concern with these systems is that the lens contacting plunger must be carefully cleaned before reuse, to avoid contamination of the IOL.

Embodiments of the present invention include an intraocular lens injector cartridge assembly configured for removably mating with an injector handpiece. The cartridge assembly is pre-loaded with an intraocular lens, and has the flexibility to be attached to a manual or automated injector. The cartridge assembly includes a lens-contacting plunger rod built into the cartridge, so that a moveable rod from the handheld-injector device engages the lens-contacting plunger rod, which in turn advances and ejects the lens. Because the cartridge and lens contacting plunger are provided as a single, disposable unit, and because the rod of the re-usable injector device never makes contact with the IOL, the likelihood of contamination is reduced over that which might occur with reusable lens-contacting plungers.

Figure 3:
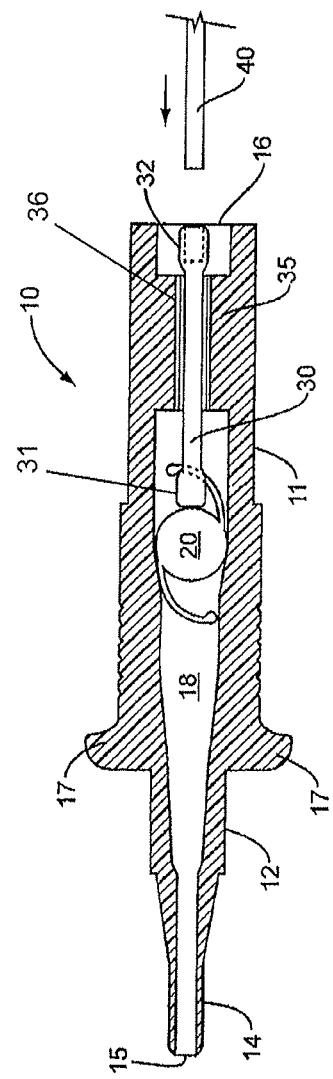
FIG. 3 is a cross-sectional view of the cartridge assembly of FIG. 1.

As seen in the exemplary embodiment pictured in FIGS. 1-3, a disposable, pre-loaded, intraocular lens injector cartridge 10 includes a tubular body 11 with a longitudinal bore 18 therein. An intraocular lens 20 is pre-installed so that it is disposed within the longitudinal bore 18, along with a lens-contacting plunger 30. The lens-contacting plunger 30 is retained at least substantially within the longitudinal bore 18, between the intraocular lens and the proximal end 16 of the cartridge 10, and may include, in some embodiments, a socket 32 for mating with an injector rod 40 of the injector handpiece (not shown). When engaged by injector rod 40, which is introduced by the injector handpiece into the proximal end 16 of the cartridge, lens-contacting plunger 30 translates along the longitudinal bore 18, folding the intraocular lens 20 as it passes through the tapering portion 12 of the cartridge, and ejecting intraocular lens 20 into a patient's eye from the distal end 15 of the cartridge. The lens-contacting plunger 30 may also include an enlarged distal portion 31. As seen in FIG. 3, the interior of the tubular body 11 may include a plunger guide feature 35 (which may be integrally formed with the tubular body, in some embodiments, or a separately installed feature in others) to keep the lens-contacting plunger rod 30 properly oriented; the plunger guide feature 35 includes a passage 36 and may also serve to retain the lens-contacting plunger rod 30 within the cartridge 10, such as by "trapping" the innermost end of the plunger rod 30 within the cartridge 10, or simply by providing sufficient friction to keep the plunger rod 30 from easily falling out of the cartridge 10.

The tubular body 11 is generally formed from any material suitable for use in eye surgery, and in some embodiments may be molded, in one or several pieces, from a suitable thermoplastic such as polypropylene. In some embodiments, the thermoplastic may contain a lubricity-enhancing agent such as those disclosed in U.S. Pat. No. 5,716,364. Nozzle 14 may be rounded, oval or elliptical in cross-section, in various embodiments, and may have a cross-sectional area as small as about one square millimeter at distal tip 15, so that the distal tip 15 may be inserted into a very small incision in the eye. In the embodiment shown in FIGS. 1-3, cartridge 10 includes a pair of grips 17 protruding from the tubular body 11; these grips allow easier manipulation of cartridge 10 and provide a mechanism for engaging the injector handpiece so that the cartridge 10 may be locked into place. Those skilled in the art will appreciate that narrowing injector portion 11 may be specially shaped to fold the intraocular lens 20 as it is pushed along the longitudinal bore 18 by lens-contacting plunger rod 30. A variety of suitable designs for the injector portion 11 are possible, including but not limited to those illustrated in U.S. Pat. No. 5,947,976 (Van Noy et al.) and U.S. Pat. No. 6,143,001 (Brown et al.); the entire contents of both of these patent documents are incorporated herein by reference.

As noted above, the tubular body 11 of the pre-loaded cartridge 10 may be formed in a single piece, in some embodiments. In such embodiments, the intraocular lens 20 and lens-contacting plunger rod 30 may be pre-installed in the cartridge 10, from the cartridge's proximal end 16, by the cartridge's manufacturer prior to shipping the device. However, other embodiments, such as the embodiment of cartridge 10 pictured in FIGS. 4A and 4B, may include an opening 42 disposed on one face of the cartridge body 11, so that the intraocular lens 20 and lens-contacting plunger rod 30 may be more easily installed. After these components are installed, the opening 42 may be closed by installing a cover 44 over the opening 42. In some embodiments, the cover 44 and tubular body 42 may be formed so that the cover 44 snaps into place; the cover 44 may form a hinged connection to the tubular body 11 at one end, in some embodiments. In other embodiments the cover 44 may be glued or otherwise fused into place after the lens-contacting plunger rod 30 and/or intraocular lens 20 are installed.

Figure 5A:
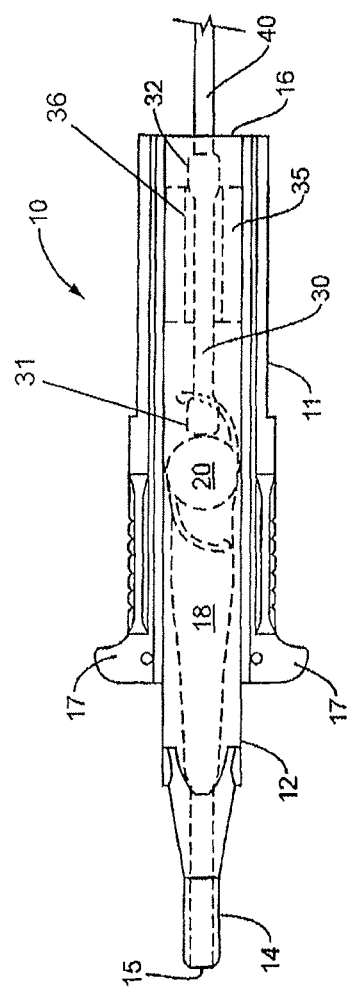
FIGS. 5A and 5B illustrate the delivery of a lens from the injector cartridge according to some embodiments of the invention.
Figure 5B:
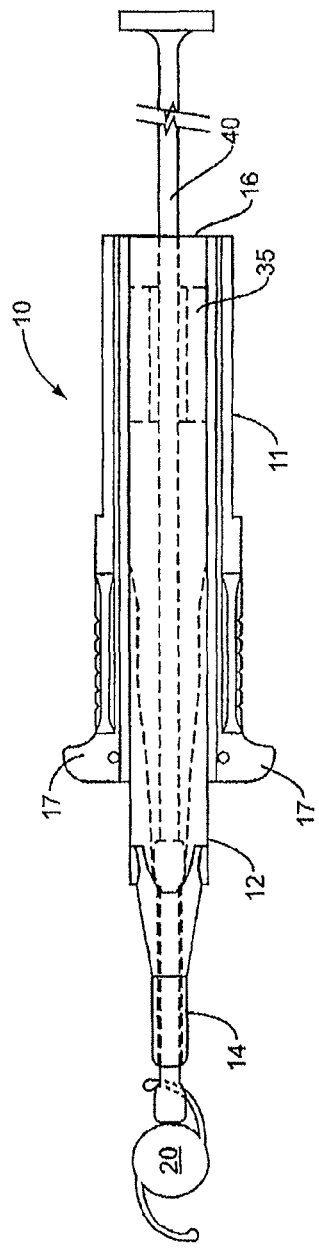

FIGS. 5A and 5B illustrate the basic operation of some embodiments of the present operation. In FIG. 5A, an injector rod 40 has been introduced by the injector handpiece into the proximal end 16 of the tubular body 11, so that it has mated with the socket 32 of the lens-contacting plunger rod 30. Further movement of the injector rod 40 causes the lens-contacting plunger rod 30 to engage the intraocular lens 20, which in some embodiments may be pre-installed in a slightly pre-folded condition. In any case, additional folding occurs as lens 20 travels through the tapering portion 12 of the cartridge body, through the nozzle 14. Finally, the intraocular lens 20 is expressed into the eye from the distal tip 15 of nozzle 14, as shown in FIG. 5B, where it unfolds into its natural shape.

Although details of the handpiece are not necessary for a full understanding of the present invention and are therefore not discussed in detail herein, those skilled in the art will appreciate that the cartridge assemblies described above are suitable for use with handpieces that include a manually activated injector rod, or with handpieces that include an electrically driven injector rod. Thus, IOL injector cartridge assemblies designed according to the concepts disclosed herein may, in some embodiments, be compatible with both sorts of handpiece. Those skilled in the art will appreciate that a further advantage of providing the cartridge, lens, and lens-contacting plunger as a single unit is the ability to dispose of the plunger after a single use, thereby reducing the likelihood of contamination that might be seen on reusable lens plungers.

The preceding description of various embodiments of an intraocular lens injection cartridge assembly and methods for using such a device was given for purposes of illustration and example. Those skilled in the art will appreciate, of course, that the present invention may be carried out in other ways than those specifically set forth herein without departing from essential characteristics of the invention. The present embodiments are thus to be considered in all respects as illustrative and not restrictive, and all changes coming within the meaning and equivalency range of the appended claims are intended to be embraced therein.

What is claimed is:

1. An intraocular lens injector cartridge assembly configured for removably mating with an injector handpiece, the cartridge assembly comprising:

a tubular body having a longitudinal bore extending between a distal end and a proximal end;

an intraocular lens disposed within said longitudinal bore; and a lens-contacting plunger rod retained substantially within said bore, between the intraocular lens and the proximal end of the tubular body, and configured for translation along the longitudinal bore upon engagement by an injector rod introduced by the injector handpiece into the proximal end of the tubular body, so that the intraocular lens is folded and ejected from the distal end of the tubular body by the translation of the lens-contacting plunger rod.

2. The cartridge assembly of claim 1, further comprising one or more grips protruding from the tubular body, for engagement with the injector handpiece.

3. The cartridge assembly of claim 1, wherein the tubular body comprises an opening disposed on a first face of the tubular body for installing at least one of the intraocular lens and the lens-contacting plunger rod, and a cover installed over said opening.

4. The cartridge assembly of claim 3, wherein the cover is connected to the tubular body by a hinge at one end of the cover.

5. The cartridge assembly of claim 3, wherein the tubular body comprises one or more retaining features proximate to the opening, and wherein the cover is configured to snap fit into the one or more retaining features.

6. The cartridge assembly of claim 1, further comprising a plunger guide disposed within the longitudinal bore and at least partially surrounding the circumference of the lens-contacting plunger rod.

7. An intraocular lens injector cartridge comprising:

a body configured to be removably mated with an injector handpiece;

a longitudinal bore extending through the body from a distal end to a proximal end; and a plunger rod disposed within the longitudinal bore, the plunger rod longitudinally moveable within the longitudinal bore and the plunger rod configured to be engaged by an injector rod of the injector handpiece.

8. The intraocular lens injector cartridge of claim 7 further comprising a plunger guide formed within the longitudinal bore, the plunger guide surrounding a circumference of the plunger rod.

9. The intraocular lens injector of claim 8, wherein the plunger rod comprises an enlarged distal portion, wherein the plunger guide defines a passage, and wherein a size of the enlarged distal portion of the plunger rod is larger than a size of the passage such that the plunger rod is retained within the longitudinal bore.

10. The intraocular lens injection cartridge of claim 7 further comprising one or more grips configured to removably secure the body to the injector handpiece.

11. The intraocular lens injection cartridge of claim 7, wherein the plunger rod comprises a socket configured to mate with the injector rod of the injector handpiece.

12. The intraocular lens injection cartridge of claim 7 further comprising an intraocular lens disposed within the longitudinal bore.

13. The intraocular lens injection cartridge of claim 12, wherein the intraocular lens is disposed between the plunger rod and a distal outlet of the body.

14. The intraocular lens injection cartridge of claim 13, wherein the longitudinal bore comprises a tapered portion, the intraocular lens disposed at a location proximal to the tapered portion.

\* \* \* \* \*